United States Patent [19]

Hutchmacher et al.

[11] Patent Number: 5,166,444
[45] Date of Patent: Nov. 24, 1992

[54] BIS(3-CYANO-3,5,5-TRIMETHYL-CYCLOHEXYLIDENE)-AZINE, A METHOD OF ITS PREPARATION AND FURTHER PROCESSING TO 3-(AMINOMETHYL)-3,5,5-TRIMETHYLCY-CLOHEXYL AMINE

[75] Inventors: Klaus Hutchmacher, Gelnhausen; Hermann Schmitt, Rodenbach, both of Fed. Rep. of Germany

[73] Assignee: Degussa AG, Fed. Rep. of Germany

[21] Appl. No.: 848,390

[22] Filed: Mar. 9, 1992

Related U.S. Application Data

[62] Division of Ser. No. 785,323, Oct. 23, 1991.

[30] Foreign Application Priority Data

Oct. 23, 1990 [DE] Fed. Rep. of Germany ....... 4033609
Jun. 14, 1991 [DE] Fed. Rep. of Germany ....... 4119577

[51] Int. Cl.$^5$ ............................................. C07C 209/48
[52] U.S. Cl. .................................... 564/491; 564/462; 558/431
[58] Field of Search ................................ 564/491, 462

[56] References Cited

U.S. PATENT DOCUMENTS 2,101,215 12/1937 Graves et al. ................ 564/462 X
2,409,061 10/1946 Norris ............................. 564/491 X
3,377,374 4/1968 Hale, Jr. et al. ................ 564/462 X
3,624,122 11/1971 Kamal et al. .................... 564/491 X

*Primary Examiner*—Joseph Paul Brust
*Attorney, Agent, or Firm*—Cushman, Darby & Cushman

[57] ABSTRACT

The invention relates to bis(3-cyano-3,5,5-trimethylcyclohexylidene)-azine (=IPN-azine), a method of its preparation by reacting 1,3,3-trimethyl-5-oxocyclohexane carbonitrile (=IPN) with a source for hydrazine in a molar ratio of essentially 2 to 1 in the presence of a solvent and to a method for the further processing of the IPN-azine to 3-(aminomethyl)-3,5,5-trimethylcyclohexyl amine (isophorone diamine=IPDA) by means of a hydrogenating azine splitting with hydrogen in the presence of an organic solvent, ammonia and of a catalytic system from the series (a) of a cobalt- or nickel-containing Raney catalyst and of a cocatalyst from the series of salts of the elements aluminum, cobalt, nickel, yttrium, lanthanum, cerium, Ru, Rh, Pd, Ir and Pt or of carrier-supported noble metals from the series Ru, Rh, Pd, Ir, Pt or b) of a carrier-supported Ru-, Pd- or Pt catalyst at a pressure of 3 to 30 MPa and a temperature of 50° to 150° C. The method of the invention concerning IPN-azine makes it possible to obtain IPDA from IPN in high yield and purity and avoids disadvantages of the previously known reductive amination of IPN.

7 Claims, 1 Drawing Sheet

BIS(3-CYANO-3,5,5-TRIMETHYL-CYCLOHEXYLIDENE)-AZINE, A METHOD OF ITS PREPARATION AND FURTHER PROCESSING TO 3-(AMINOMETHYL)-3,5,5-TRIMETHYLCYCLOHEXYL AMINE

This is a division of application Ser. No. 07/785,323, filed Oct. 23, 1991.

The present invention relates to a new compound, bis(3-cyano-3,5,5-trimethylcyclohexylidene)-azine, to a method of preparing it from 1,3,3-trimethyl-5-oxo-cyclohexanecarbonitrile and to converting it to 3-(aminomethyl)-3,5,5-trimethylcyclohexyl amine.

BACKGROUND OF THE INVENTION 3-(aminomethyl)-3,5,5-trimethylcyclohexyl amine (referred to herein as "isophorone diamine"), is used as a starting material for the preparation of isophorone diisocyanate, as an amino component for polyamides and as hardener for epoxide resins.

Isophorone diamine (IPDA) has been obtained by the reductive amination of 1,3,3-trimethyl-5-oxo-cyclohexane carbonitrile, (referred to herein as "isophorone nitrile" and as "IPN"), in the presence of ammonia and conventional hydrogenation catalysts. The isophorone nitrile used as starting material can be obtained by reaction of hydrogen cyanide and isophorone—cf. published German patent application P 39 42 371.9.

According to the method of German patent 12 29 078, ammonia and IPN are added in a molar ratio of 10-30 to 1 in order to obtain IPDA. However, in addition to the desired IPDA, a rather large amount of byproducts are produced, such as, in particular, 3-(aminomethyl)-3,5,5-trimethylcyclohexanol (=isophorone amino alcohol (IPAA)), 1,3,3-trimethyl-6-azabicyclo-3,2,1-octane and dihydroisophoryl amine. By way of example, a yield of up to 81.4% IPDA is disclosed but further purity data is absent. According to various sources, this yield has proved to be non-reproducible.

An attempt has been made to increase the yield of IPDA and to minimize the formation of IPAA in the process of German patent 12 29 078. According to the disclosure of published German patent application DE-OS 30 11 656, the method was changed by, in a first stage, converting IPN, without catalyst but with excess ammonia, into 1,3,3-trimethyl-5-imino-cyclohexanecarbonitrile. The latter was hydrogenated in a second stage to IPDA. A considerable excess of ammonia had to be used in the second stage. This mode of operation makes it necessary to use a complicated pressure distillation to recover and recycle the ammonia. According to the example given, a reaction yield of only 83.7% was achieved in the method of DE-OS 30 11 656, in spite of a ratio of approximately 5 kg ammonia per 1 kg IPN; no data is given about the ultimate yield of IPDA and its purity.

Published German patent application DE-OS 30 21 955 discloses that there was a further need to improve the methods of the foregoing disclosures. According to reference Example 1 of DE-OS 30 21 955, an IPDA yield of only 48% is achieved in spite of an IPN/NH$_3$ volumetric ratio of 1 to 10 in the method of German patent 12 29 078. According to reference Examples 2 and 3 of DE-OS 30 21 955, carried out by the method of DE-OS 30 11 656, it was possible to obtain a yield of approximately 70% and 90%. However, the high yield required a long reaction time for the first stage and an IPN/NH$_3$ volumetric ratio of 1 to 10 in the second stage. Thus, in addition to the disadvantage of the high excess of ammonia, there is also an economically significant reduction of the space-time yield.

DE-OS 30 21 955 disclosed that it was possible to reduce the long reaction time for the first stage—imine formation—in the method of DE-OS 30 11 656 by using an imine formation catalyst. However, it still was necessary to use a volumetric ratio of isophorone nitrile to ammonia of 1:10 to 20 in the second stage, and therewith an expensive system for pressure distillation, for the hydrogenation in the second stage. A further disadvantage is the fact that the reaction is complicated to carry out.

The method of published Japanese patent application JP-A 62-123154 involves the reductive amination of IPN for the preparation of IPDA, in which an attempt was made to reduce the required excess of ammonia and to eliminate the preliminary reduction of the carrier-supported catalyst. It should be possible, according to this method, upon using 1 to 20 times, preferably 5 to 10 times the molar amount of ammonia, relative to IPN, as well as Raney cobalt as catalyst, a pressure of 50 to 150 bars and a temperature of 50° to 150° C., to obtain IPDA in a high yield—the IPDA component in the reaction mixtures of the examples was approximately 83–89%, the IPAA component 4–6% (GC areal %). Considering the high amount of IPAA, which is difficult to separate, a not inconsiderable yield loss of IPDA must be dealt with in the purification by distillation. When the present inventors repeated the method of JP-A 123154, the statements of JP-A 62-123154 could not be confirmed. As is apparent from reference Examples 1 and 2 herein, IPN is hydrogenated only to an insufficient extent, to IPDA, under the conditions described in JP-A 62-123154.

It is clear from the state of the art described above that the desired isophorone diamine (IPDA) can only be obtained in good yield, with limited unavoidable accumulation of isophorone amino alcohol (IPAA), by the reductive amination of isophorone nitrile with ammonia and hydrogen via the intermediate product 1,3,3-trimethyl-5-imino-cyclohexanecarbonitrile, if ammonia was used in a very great excess. This excess of ammonia necessitated a complicated system, with apparatus for pressure distillation and recovery of the imine formation catalyst.

SUMMARY OF THE INVENTION

The object of the present invention is to provide a new method of preparing isophorone diamine from isophorone nitrile which minimizes the disadvantages of the previously known methods and which, in particular, reduces the quantity of ammonia to such an extent that pressure distillation is not required. A further object is to provide such a method in which IPDA is formed in high yield and practically no IPAA is formed.

It has been found that, during the reaction of isophorone nitrile with a source of hydrazine, in a molar ratio of essentially 2:1, a previously unknown azine, namely, bis(3-cyano-3,5,5-trimethylcyclohexylidene)-azine (referred to herein as "IPN-azine") is produced in practically quantitative yield. The IPN azine can be hydrogenated in the presence of ammonia and catalysts to isophorone diamine (see reaction scheme).

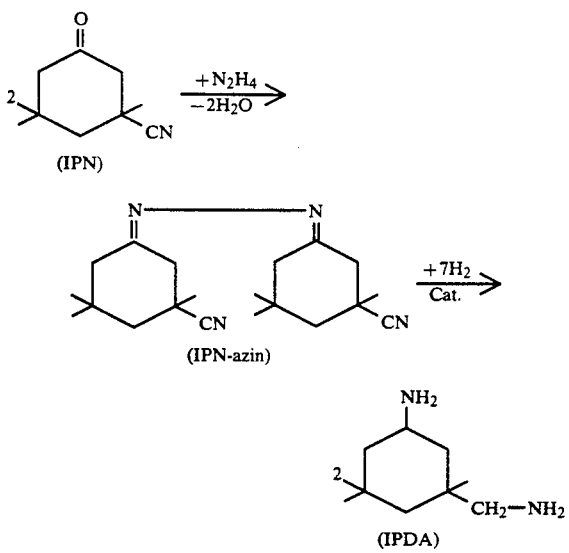

The intermediate product IPN-azine, which can be isolated by means of conventional methods from the reaction mixture, is a novel compound and its structure has been confirmed by analytical and spectroscopic methods. It could not have been expected that very pure isophorone diamine can be obtained in the further processing of IPN-azine without the unavoidable accumulation of byproducts.

In accordance with the present invention IPN-azine is prepared by reacting 1,3,3-trimethyl-5-oxo-cyclohexane carbonitrile (=IPN) and a source for hydrazine in a molar ratio of essentially 2:1 in the presence of a solvent and, to the extent desired, the IPN-azine is isolated from the reaction mixture with conventional methods.

Potential sources for hydrazine are hydrazine, hydrazine hydrate and aqueous solutions of the same in different concentrations and hydrazine salts. Hydrazine hydrate and aqueous solutions thereof are especially preferred. In the instance in which hydrazine salts are used, a subsequent neutralization of the salt formed during the reaction is necessary. Therefore, hydrazine salts are less preferable than hydrazine and hydrazine hydrate because of the accumulation of salt.

Because of the formula of IPN-azine, two moles of isophorone nitrile are required per mole of source for hydrazine. The molar ratio "essentially 2:1" implies a ratio of, preferably, 2:1, but either of the reactants can be used in up to a 10% excess.

The reactants are brought together in the presence of a solvent, during which time the reaction mixture is advantageously agitated. Both reactants can be supplied simultaneously to the reaction vessel. The solvent may be introduced into the reaction vessel before the reactants are added, or it may be introduced with at least one of the reactants. Of course, one of the reactants can also be put in the reaction vessel with the solvent and brought to reaction by adding the second reactant. The reaction can be carried out either discontinously or continuously.

The reaction is exothermic. The reaction temperature is not critical and is preferably in a range of 20° C. to 120° C. It is especially preferable if the reaction takes place at the boiling temperature of the solvent.

Solvents which may be used are solvents which are inert to IPN and hydrazine as well as aqueous and also organic solvents; the latter are preferred. The solvent functions as a liquid reaction medium. At least one of the reactants should be at least partially, preferably entirely soluble in the solvent; both reactants are preferably at least partially and advantageously completely soluble in the solvent—this property can be readily determined by a preliminary test. It is especially advantageous to select such solvents in which the IPN-azine produced is only slightly soluble and therefore precipitated at least partially as a solid during the reaction—this accelerates the reaction by shifting the equilibrium toward azine formation. Solvent mixtures, even aqueous-organic ones, can be used but do not offer any advantages. Solvents with a boiling point under 120° C. are preferable. Lower mono- or bivalent alcohols are especially suitable, especially monovalent $C_1$ to $C_4$ alcohols and aliphatic or cyclic ethers with up to 6 carbon atoms; other possibilities are also aliphatic or cycloaliphatic hydrocarbons such as e.g. cyclohexane. It is especially advantageous for the preparation of azine to use the solvent which also is suitable for the further processing to IPDA.

The IPN-azine can be isolated from the reaction mixture by distilling off the solvent or, if the IPN-azine is hardly soluble in the solvent, by solid-liquid phase separation. If necessary, the isolation can be followed by further purification, e.g. by washing or recrystallization. Since the reaction is essentially quantitative and hardly any byproducts are formed, isolation and purification prior to further processing to IPDA are generally unnecessary.

The further processing of the IPN-azine to isophorone diamine (IPDA) is carried out by hydrogenating the IPN-azine with hydrogen in the presence of an organic solvent, ammonia and a catalytic system from the series a) of a cobalt- or nickel-containing Raney catalyst and of a cocatalyst from the series of salts of the elements aluminum, cobalt, nickel, lanthanum, yttrium, cerium, Ru, Rh, Pd, Ir and Pt or of carrier-supported noble metals from the series Ru, Rh, Pd, Ir, Pt or b) of a carrier-supported ruthenium-, palladium- or platinum catalyst at a pressure of 3 to 30 MPa and a temperature of 50° to 150° C. The reaction mixture is worked up by distillation after the solids have been separated off.

The hydrogenation of the IPN-azine takes place with hydrogen, during which process the nitrile groups are hydrogenated and the azine group split and hydrogenated. The preferred pressure range is 8 to 15 MPa, the preferred temperature 90° to 120° C. Both the presence of ammonia as well as the use of the catalytic system (a) or (b) are essential. The cocatalyst of catalytic system (a) increases on the one hand the hydrogenation activity of the Raney catalysts and on the other hand makes the azine splitting possible.

The hydrogenation of the IPN-azine to IPDA can take place either discontinuously or also continuously and conventional hydrogenation reactors such as those used for hydrogenations employing suspension catalysts can be used; agitated autoclaves and loop-type bubble columns are mentioned as examples.

Those solvents can be considered for use which exhibit a sufficient solvent power for IPN-azine and IPDA at the hydrogenation temperature selected. After the hydrogenation, IPDA should be completely in solution in order to facilitate separation of solids, that is, the catalyst and, if necessary, cocatalyst, by means of simple filtration from the reaction mixture. The following are suitable possibilities, for example: Lower alcohols, especially monovalent $C_1$ to $C_4$ alcohols, aliphatic and cycloaliphatic mono- and diethers, especially those with up to 6 carbon atoms, but also generally aliphatic and cycloaliphatic hydrocarbons such as cyclohexane. Those solvents are preferably selected which can be readily distilled off from the reaction mixture, that is, which exhibit a boiling point below 120° C. The solvent must be stable under the conditions of hydrogenation.

As has already been explained, the presence of ammonia is essential. Amounts of 50 to 500 g $NH_3$ per kg IPN-azine have been found in particular to be satisfactory; however, smaller and larger amounts can also be used. An increase of the $NH_3$ amount to above 2 kg per kg IPN-azine makes little sense for economic considerations, because the space-time yield and the purity of the IPDA are not improved further. An $NH_3$ amount below 50 g per kg IPN-azine reduces the yield of IPDA and the purity of the IPDA crude product.

In principle, hydrazine can also be used instead of ammonia; however, this alternative is considered to be less advantageous.

The Raney catalysts which can be prepared from NiAl- and CoAl alloys, which can also contain other metals in addition such as e.g. manganese, in a generally known manner and which are also commercially available are used as catalysts of catalytic system (a).

In catalytic system (a), two types of cocatalysts, namely, salts of the elements Al, Co, Ni, Y, lanthanides Ru, Rh, Pd, Ir, Pt and carrier-supported noble metals of the series Ru, Rh, Pd, Ir, Pt are useful. Salts of mineral acids or organic acids are suitable among the salts, which are added in the form of a solution or as a solid to the reaction batch or which are brought together with the catalyst in advance; halides and acetates in anhydrous or hydrous form are preferred. Chlorides of Al, Co, Ni, Y, La, Ce, especially from Co and Ni, are particularly advantageous. The cocatalyst salt is customarily added in an amount of 0.01 to 0.5 mole, especially 0.05 to 0.2 mole per mole Raney nickel or Raney cobalt. The carrier-supported noble metal cocatalysts are those on finely divided carriers, such as e.g. on activated carbon, silica, aluminum oxide or silicatic substances, which can be prepared in a known manner or are commercially obtainable. Catalytic system (b) has the advantage that it can be used without cocatalyst. Carrier-supported ruthenium catalysts are preferred over the Pd- and Pt catalysts because of higher yields and product purity. The finely divided substances known to the expert in the art such as e.g. carbon, aluminum oxide, silicates as well as oxides of Ti, Zr, Sn, La, Ce are potential carrier materials; carbon and aluminum oxide are especially preferred. Carrier-supported noble metal catalysts can be prepared in a known manner or can also be obtained in part commercially.

The splitting in a hydrogenating manner of azines or aromatic aldehydes during the hydrogenation with hydrogen in acetate solution using Rh on activated carbon as catalyst is per se known (see JP 01203355 Az (1989)=Chem. Abstr. 112 (9): 76465 g). However, this method is not successful in the desired hydrogenation of IPN-azine to IPDA. It was therefore surprising that carrier-supported Ru-, Pd- and Pt-catalysts render the desired possible, i.e., simultaneous hydrogenation and azine splitting in the method of the invention. An azine splitting with the Raney catalyst/salt cocatalyst system has never been described or rendered obvious in the past.

It is possible to obtain isophorone diamine in a high yield and in a simple manner by means of the hydrogenation of IPN-azine in accordance with the invention, which IPN-azine, as has already been explained, is readily obtainable from IPN and is used with advantage in the form of a suspension obtained when it is prepared. The previously necessary high excess of $NH_3$ and the associated pressure distillation are not necessary. The IPDA raw product, obtained after the hydrogenation, separation of the catalyst and cocatalyst and distilling off of the ammonia and of the solvent, is free of isophorone amino alcohol, which is considered to be problematic. Further purification of the IPDA raw product is readily possible with customary distillation methods.

DETAILED DESCRIPTION OF PREFERRED EMBODIMENTS

Figure 1:
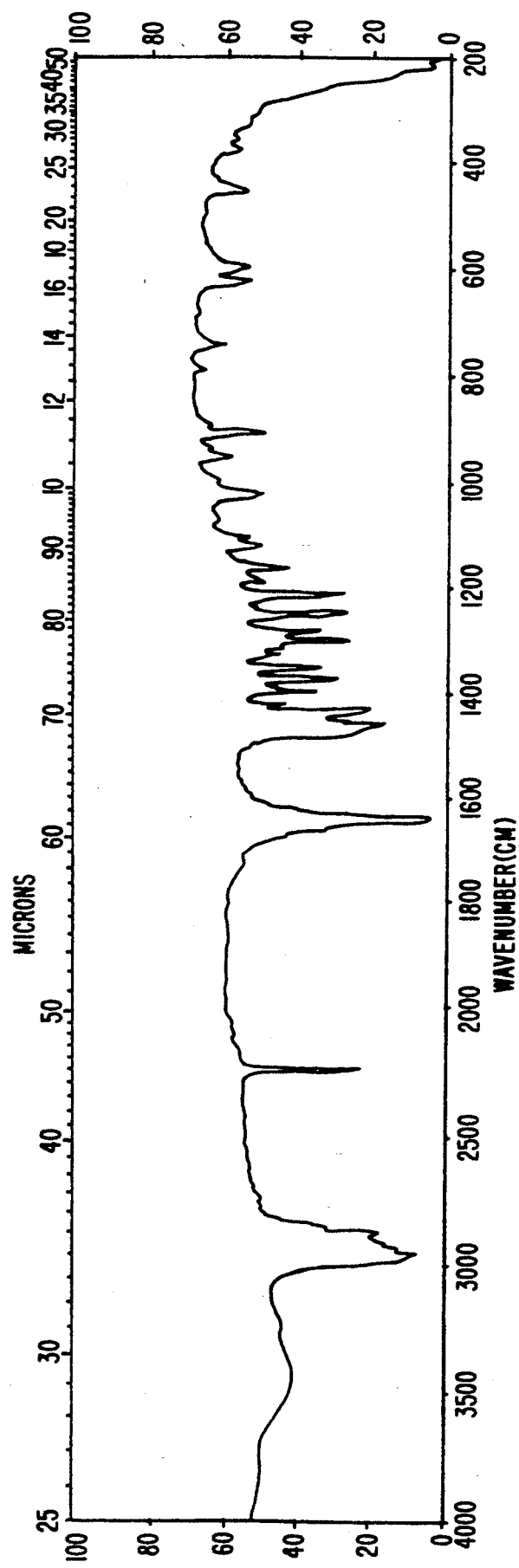

The invention is illustrated by the following examples:

EXAMPLE 1

Preparation of IPN-azine from IPN 495.4 g (3 moles) isophorone nitrile are added to 1200 ml methanol at room temperature (=RT). 93.9 g (1.5 moles hydrazine hydrate (80%) is added with agitation; the reaction solution is heated to a boil. The mixture is allowed to cool down under agitation, during which the IPN-azine precipitates. After filtration and subsequent washing with cold methanol, it is dried in a vacuum at 60° C. IPN-azine 454 g, corresponding to 92.7% of theory. Melting point 191° to 194° C. Elementary analysis.

C calc.: 73.58; H calc. 9.28; N calc. 17.15; C obs. 73.40; H obs. 9.35; N obs. 17.10.

IR spectrum: $V_{C=N}$ 2230 $cm^{-1}$; $V_{C=N}$ 1680 $cm^{-1}$

The IPN-azine was characterized by $^1H$- and $^{13}C$-NMR spectra in addition to IR spectrum—see FIG. 1/1.

EXAMPLE 2

Preparation of IPN-azine from isophorone, HCN and $N_2H_4.H_2O$ without isolation of the IPN Equipment: 2 liter three-neck flask, reflux condenser, thermometer, dropping funnel, agitator 752 ml (5 moles) isophorone and 3 g LiOH are placed in a flask and heated with agitation to 130° C. 118 ml (3 moles) hydrogen cyanide is allowed to drop in drop-by-drop within 15 minutes, during which time the temperature rises to 150° to 155° C. After a brief subsequent agitation at room temperature, the mixture is adjusted to a pH of 2-3 with HCl. Then excess isophorone is distilled off at reduced pressure and an internal temperature up to 145° C.-254.8 g, boiling point$_{14}$ 59°-97° C. 1.2 liters methanol are added to the distillation residue containing essentially IPN and the Li salts are then filtered off and subsequently washed with 100 ml methanol. 75 ml (1.5 moles) hydrazine hydrate (100%) is added drop-by-drop during 20 minutes to the combined methanol phases, during which time the temperature rises to approximately 35° C. and the crystallization of the IPN-azine begins under agitation and cooling. After 3 hours it is filtered off at 20° C., finally washed and dried. IPN-azine 415.4 g=84.8% of theory; melting point 192°-194° C., elementary analysis.

C calc.: 73.58; H calc. 9.26; N calc. 17.15; C obs. 73.10; H obs. 9.86; N obs. 17.01.

A further 30 g=6.1% of theory IPN-azine can be obtained from the filtrate.

EXAMPLE 3

163 g (0.50 mole) IPN-azine are dissolved in a 2 liter autoclave with gas agitator in 850 ml methanol and 150 ml anhydrous liquid ammonia. After the addition of 12.5 g Raney nickel and 6 g cobalt chloride hexahydrate as cocatalyst, hydrogen is introduced until the pressure reaches 100 bars while the mixture is agitated and heated to 110° C.

After the conclusion of hydrogenation, the catalyst is filtered off; then ammonia and the solvent are drawn off and the residue distilled in a vacuum via a column.

Main fraction: 155.2 g (91.2% of theory) IPDA; $bp_{0.3}$: 74°–76° C. Residue: 3.2 g.

The purity of the main fraction, determined with gas chromatography, is 99.2% and it contains no IPAA.

(GC conditions: Capillary column DB5; length 30 m; Injection block temp.: 250° C.; Detector temp.: 250° C.; Temperature program 70°–270° C.)

EXAMPLE 4

Example 3 is repeated, but with 1.5 moles=489.6 g IPN-azine, 2.65 l methanol and 0.35 l anhydrous ammonia; 35.0 g Raney cobalt and 5.0 g cobalt chloride hexahydrate were used as catalyst. Yield 476.8 g (93.5% of theory) IPDA.

EXAMPLE 5

Example 4 is repeated, but with 200 ml ammonia and 2.8 l methanol. Yield of IPDA: 454.4 g (89% of theory); purity 99.0%, free of IPAA.

EXAMPLE 6

Example 4 is repeated, but with 50 ml ammonia and 2.9 l methanol. Yield of IPDA 410 g (80.3% of theory); purity 98.3%.

EXAMPLE 7

Example 4 is repeated, but with 2.8 l methanol and 75 ml hydrazine hydrate (100%) instead of ammonia. Yield 357 g (70% of theory) IPDA; product purity 98.3%.

EXAMPLE 8 not in accordance with the invention

Example 5 was repeated but the cocatalyst cobalt chloride hexahydrate was omitted. Yield of IPDA 352 g (69% of theory) with a purity of 98.2%. Considerable amounts of bis(3-aminomethyl-3,5,5-trimethyl-cyclohexylidene)-azine were in the residue.

EXAMPLE 9

495.4 g (3 moles) isophorone nitrile are suspended in 1.3 l methanol at 10° C., then 75 ml (1.5 moles) hydrazine hydrate (100%) are slowly added; the temperature rises to 34° C. Agitation of the mixture continues until the IPN-azine completely precipitates. The suspension obtained in this manner is transferred into a 5 l agitated autoclave, combined with 1250 ml methanol and 0.45 l anhydrous ammonia and hydrogenated in the presence of 35 g Raney nickel and 12.5 g nickel chloride hexahydrate at 110° C. and 100 bars hydrogen pressure. After the mixture has cooled off, the catalyst is filtered off, the solvent drawn off and the residue distilled in a vacuum.

Yield: 475 g (93% of theory) IPDA content 99.3%; Residue: 24.4 g.

EXAMPLE 10

Preparation of IPDA from isophorone via IPN (according to published German patent application P 39 42 371.9) and IPN-azine-"hot-pot variant"

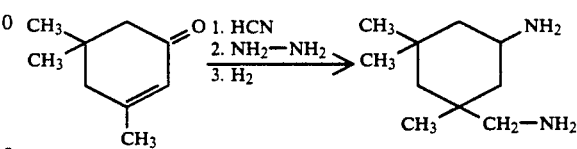

Additives: 752 ml isophorone (=5 moles) (IP)
3 g: LiOH
118 ml: hydrogen cyanide (=3 moles) conc. HCl
1.2 l: methanol
75 ml: hydrazine hydrate (=1.5 moles)
1 l: $NH_3$, liquid
100 g: Raney cobalt
50 g: $CoCl_2.6H_2O$ The reaction of the isophorone with HCN takes place according to Example 2. After the isophorone excess has been distilled off—270 g, $bp_{14}$ 54°–95° C., internal temperature 145° C.—, the distillation residue is treated further as in Example 2 and converted to IPN-azine. The IPN-azine suspension was transferred into a 5 l agitated autoclave and combined with the catalyst, cocatalyst and 1.35 l methanol; then 0.45 l ammonia (liquid) and then hydrogen was added under pressure. The mixture was hydrogenated at 110° C. while maintaining a pressure of 10 MPa until the end of the absorption of hydrogen. After the end of the absorption of $H_2$, the pressure was released, the solid filtered off from the solution and the residue washed with 200 ml methanol. The solution was freed of methanol in a vacuum and the bottom distilled in a high vacuum via a 30 cm Vigreux column:

| Forerun: | 1.1 g | $bp_{0.1}$: to 75° C. |
|---|---|---|
| Main fraction: | 460 g = 90% of theory | $bp_{0.3}$: 75–78°C. |
| Residue: | 28.9 g | internal temp. to 140° C. |

The main fraction consisted of isophorone diamine (IPDA) in a purity (GC) of 99.1%.

EXAMPLES 11 TO 13

IPN-azine was hydrogenated to IPDA using the method of Example 3 but using the cocatalysts indicated in the table. The cocatalysts, their amount and the yield of IPDA and the purity are given in the table.

TABLE

| Example No. | 11 | 12 | 13 |
|---|---|---|---|
| Cocatalyst | $CeCl_3.7H_2O$ | $AlCl_3$ | $PdCl_2$ |
| Amount cocat. (g) | 6.5 | 2.4 | 3.8 |
| Yield IPDA (% of theory) | 89.3 | 88.1 | 89.6 |
| Purity IPDA (%) | 98.8 | 98.5 | 98.6 |

EXAMPLE 14

IPN-azine was hydrogenated according to Example 3 but using a carrier-supported noble metal—40 g 5% Rh on carbon with 52% water—as cocatalyst. 150 g IPDA (=88.1% of theory) were obtained at $bp_{0.3}$ 75°–78° C.; purity 99.1%.

EXAMPLE 15

The hydrogenation of the IPN-azine took place according to Example 3; however, no cocatalytically active salt was added but rather such a salt was formed by the addition of 1 ml acetic acid in situ from a part of the Raney catalyst. IPDA was obtained in a yield of 88.7% of theory with a purity of 99.3%.

EXAMPLE 16

The hydrogenation took place according to Example 3 but using ethanol as solvent instead of methanol: IPDA distillation 153.8 g=90.4% of theory; IPDA content: 99.4%.

EXAMPLE 17

8.1 kg (24.85 moles) IPN-azine are placed with 33 kg methanol and 5 kg ammonia in a circulating reactor and heated at a hydrogen pressure of 7 MPa to 110° C. After the addition of 0.59 kg Raney Ni and 0.207 kg nickel chloride hexahydrate as cocatalyst, the mixture is hydrogenated until the end of the absorption of hydrogen (2.5 hours). After the mixture has cooled, the catalyst is filtered off and the solvent drawn off with the ammonia; the residue is fractionated in a vacuum.

Main fraction: 7.95 kg (94.1% of theory) IPDA; $bp_{0.3}$: 75°–77° C.; purity 99.3%.

Reference example 163.2 g IPN-azine, 250 ml methanol, 350 ml dioxane, 17.5 g Raney nickel and 4.2 g $NiCl_2.6H_2O$ are agitated in a 2 l agitated autoclave at 110° C. and 100 bars $H_2$ until the end of the absorption of $H_2$. 80.7 g IPDA=47.4% of theory is obtained after the workup.

EXAMPLE 18

163.2 g (0.50 mole) IPN-azine are dissolved in a 2 l autoclave with gas agitator in 850 ml methanol and 150 ml anhydrous liquid ammonia. After the addition of 50 g 5% Ru/C and 70 ml water, hydrogen is pressured up to 10 MPa under agitation and the mixture is heated to 110° C. After the end of the hydrogenation, the mixture is cooled the pressure removed; then the catalyst is filtered off, the ammonia and the solvent drawn off and the residue distilled under vacuum via a column.

Main fraction: 144.6 g (85% of theory) IPDA; $bp_{0.3}$: 74°–77° C.

Residue: 8.0 g.

The filtered-off catalyst was resuspended in 70 ml water without the supplementation of filtration losses and used for further tests of the same batch size.

| Number of the renewed batch | IPDA yield |
| --- | --- |
| 2. | 86.1% of theory |
| 3. | 86.0% of theory |
| 4. | 87.5% of theory |
| 5. | 86.0% of theory |
| 6. | 89.0% of theory |
| 7. | 88.3% of theory |
| 8. | 86.7% of theory |

The product purities were at 98–99% in each instance (GC determination). The catalytic cycles were able to be continued even further without yield losses.

What is claimed is:

1. A method for converting bis(3-cyano-3,5,5-trimethylcyclohexylidene)-azine to 3-(aminomethyl)-3,5,5-trimethylcyclohexyl amine which comprises hydrogenating bis(3-cyano-3,5,5-trimethylcyclohexylidene)-azine with hydrogen in the presence of an organic solvent, ammonia and a catalytic system selected from the group consisting of
   a) a cobalt- or nickel-containing Raney catalyst and a cocatalyst selected from the group consisting of the salts of the elements aluminum, cobalt, lanthanum, yttrium, cerium, Ru, Rh, Pd, Ir and Pt or of carrier-supported noble metals selected from the group consisting of Ru, Rh, Pd, Ir, Pt, and
   b) a carrier-supported ruthenium-, palladium- or platinum catalyst at a pressure of 3 to 30 MPa and a temperature of 50° to 150° C. separating the solids from the reaction mixture and distilling the reaction mixture after the solids have been separated off.

2. A method according to claim 1 in which the hydrogenation is carried out at a pressure of 3 to 15 MPa and a temperature of 80° to 120° C.

3. A method according to claim 1 or claim 2 in which 50 to 500 g ammonia are used per kg IPN-azine.

4. A method according to claim 1 or claim 2 in which Raney nickel or Raney cobalt is used as catalyst and in which at least one chloride of the elements Al, Co, Ni, Y, La and Ce is used as cocatalyst.

5. A method according to claim 1 or claim 2 in which a $C_1$ to $C_4$ alcohol, an ether with up to 6 carbon atoms or an aliphatic or cycloaliphatic hydrocarbon is used as solvent.

6. A method according to claim 1 or claim 2 in which bis(3-cyano-3,5,5-trimethylcyclohexylidene)-azine is used in the form of a suspension.

7. A method according to claim 1 or claim 2 in which a carrier-supported ruthenium catalyst is used as catalytic system (b) and the carrier is carbon or aluminum oxide in finely distributed form.

* * * * *